United States Patent
Squara

(10) Patent No.: US 11,413,140 B2
(45) Date of Patent: *Aug. 16, 2022

(54) HEART VALVE PROSTHESES

(71) Applicant: Pierre Squara, Enghien (FR)

(72) Inventor: Pierre Squara, Enghien (FR)

( * ) Notice: Subject to any disclaimer, the term of this patent is extended or adjusted under 35 U.S.C. 154(b) by 455 days.

This patent is subject to a terminal disclaimer.

(21) Appl. No.: 16/527,934

(22) Filed: Jul. 31, 2019

(65) Prior Publication Data

US 2019/0350704 A1    Nov. 21, 2019

Related U.S. Application Data

(62) Division of application No. 14/410,373, filed as application No. PCT/IB2012/001630 on Jun. 22, 2012, now Pat. No. 10,413,402.

(51) Int. Cl.
*A61F 2/24* (2006.01)

(52) U.S. Cl.
CPC .......... *A61F 2/2412* (2013.01); *A61F 2/2403* (2013.01); *A61F 2/2409* (2013.01); (Continued)

(58) Field of Classification Search
CPC .... A61F 2/2403; A61F 2/2409; A61F 2/2412; A61F 2/2427; A61F 2250/0031; A61F 2250/0059

See application file for complete search history.

(56) References Cited

U.S. PATENT DOCUMENTS

2005/0234541 A1  10/2005  Hunt
2007/0142907 A1   6/2007  Moaddeb et al.
(Continued)

FOREIGN PATENT DOCUMENTS

CN    1701770 A   11/2005
CN  101969885 A    2/2011

OTHER PUBLICATIONS

International Search Report for International Application No. PCT/IB2012/001630, dated Mar. 22, 2013.
(Continued)

*Primary Examiner* — Dinah Baria
(74) *Attorney, Agent, or Firm* — Heslin Rothenberg Farley & Mesiti P.C.; Victor A. Cardona, Esq.

(57) ABSTRACT

A prosthetic heart valve includes a prosthetic valve annulus and at least one prosthetic valve leaflet member including at least one coaptation surface configured for cooperating with at least one corresponding coaptation surface of the prosthetic heart valve. At least one valve leaflet member is displaceable by blood flow between a closed position and an open position to produce, correspondingly, a contact and a separation of cooperating coaptation surfaces. In the open position the separation of the cooperating coaptation surfaces enables the blood flow through the orifice in a first direction, and in the closed position the contact of the cooperating coaptation surfaces prevents the blood flow through the orifice in a second direction, opposite to the first direction. The prosthetic heart valve includes at least one device configured for preventing at least in part the contact between cooperating coaptation surfaces, so that a blood regurgitation in the second direction is enabled, wherein the at least one device is configured for ceasing its action after a predetermined amount of time.

11 Claims, 8 Drawing Sheets

(52) U.S. Cl.
CPC .... *A61F 2/2427* (2013.01); *A61F 2250/0031* (2013.01); *A61F 2250/0059* (2013.01)

(56) References Cited

U.S. PATENT DOCUMENTS

| | | |
|---|---|---|
| 2009/0138078 A1 | 5/2009 | Paul et al. |
| 2009/0164029 A1 | 6/2009 | Stocker et al. |
| 2009/0276039 A1 | 11/2009 | Meretei |
| 2011/0288621 A1 | 11/2011 | Agnew |
| 2016/0008128 A1 | 1/2016 | Squara |

OTHER PUBLICATIONS

Chinese Office Action from corresponding Chinese Application No. 201280075403.1 dated Nov. 4, 2015.

Japanese Office Action, dated May 10, 2016, together with English translation, for corresponding Japanese Patent Application No. 2015-517865.

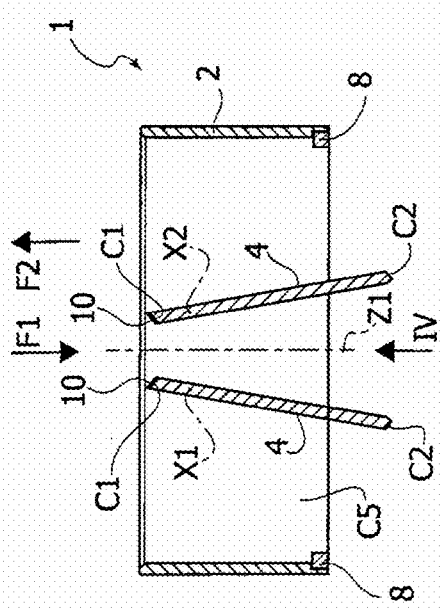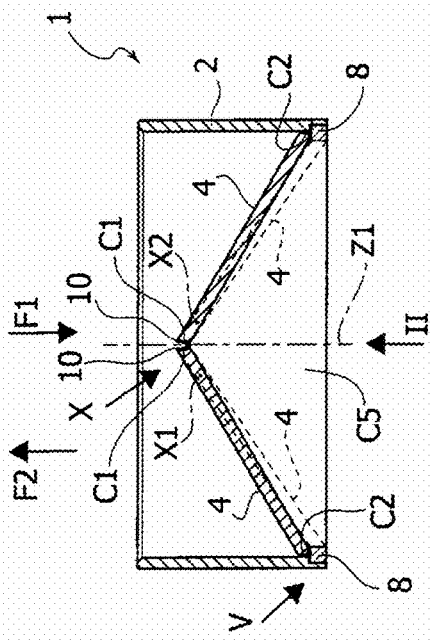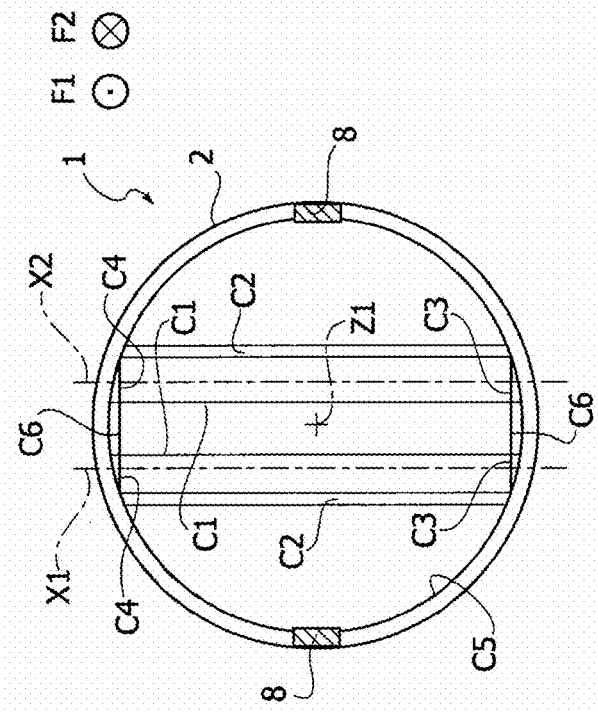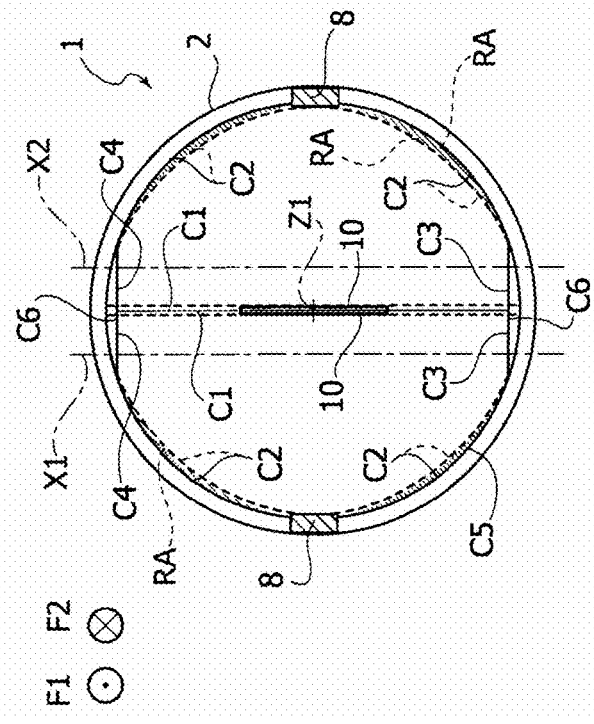

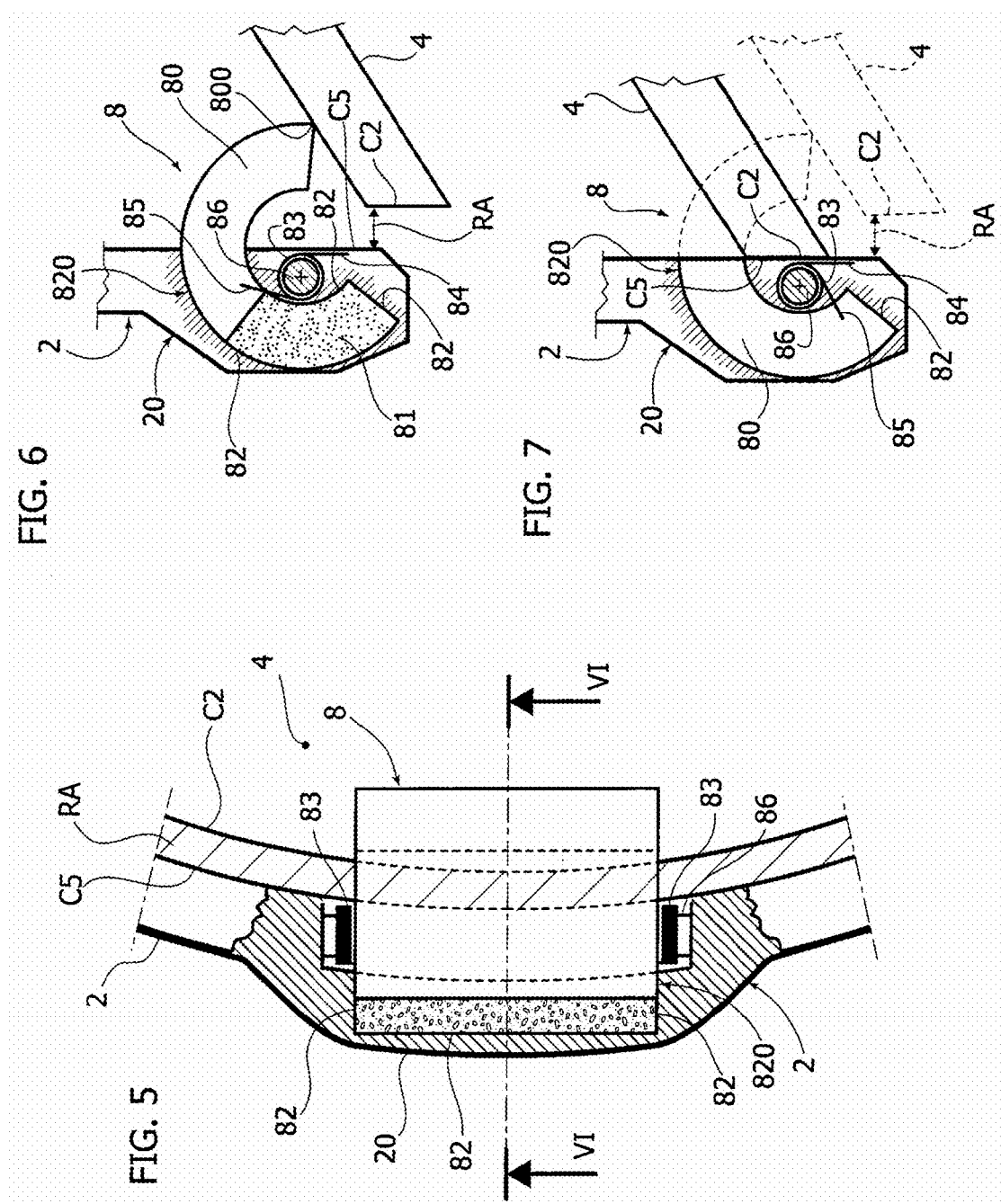

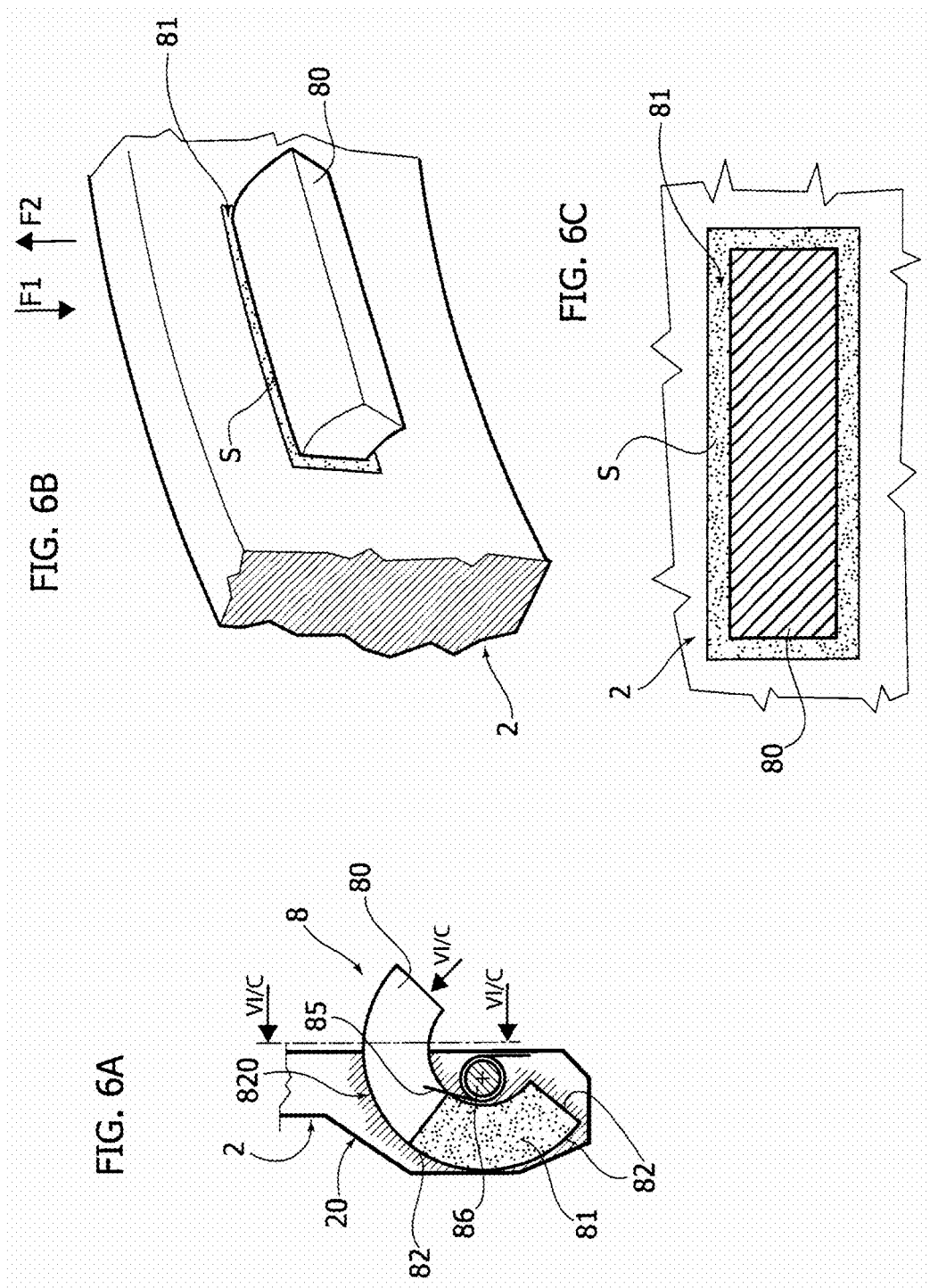

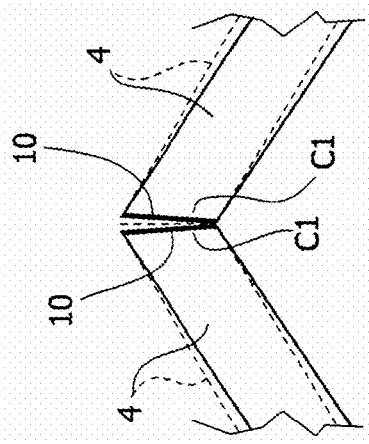
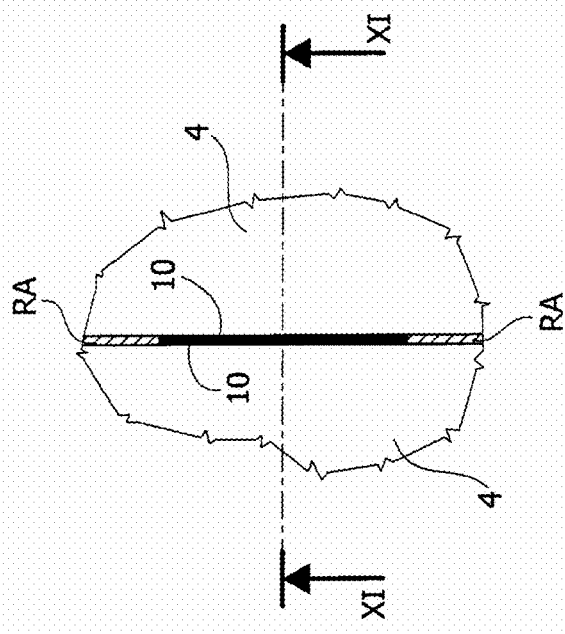

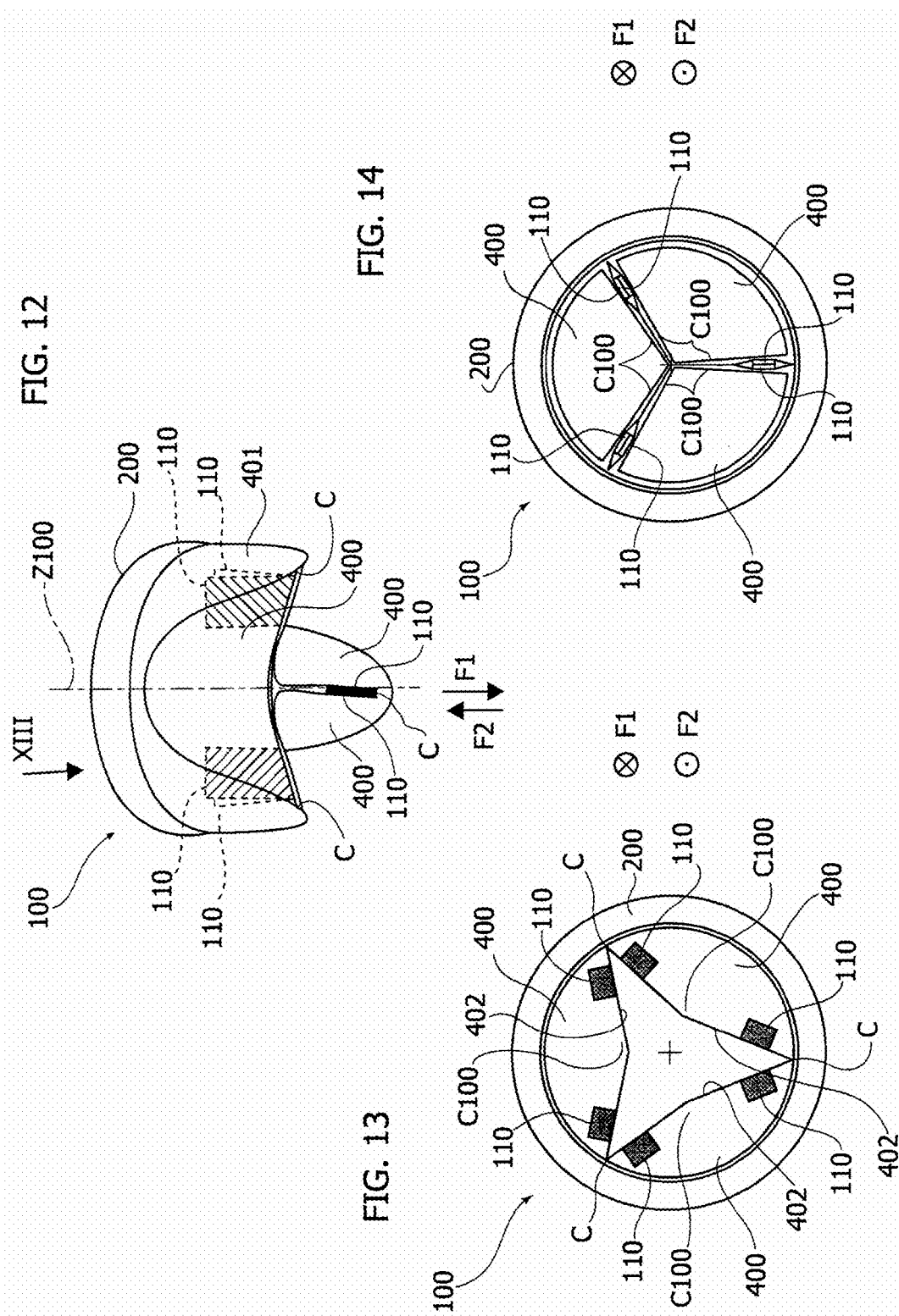

HEART VALVE PROSTHESES

CROSS REFERENCE TO RELATED APPLICATIONS

This application is a divisional patent application of U.S. patent application Ser. No. 14/410,373 filed on Dec. 22, 2014 which is a national stage filing under section 371 of International Application No. PCT/IB2012/001630, filed on Jun. 22, 2012, and published in English on Dec. 27, 2013, as WO 2013/190344, the entire disclosure of this application being hereby incorporated herein by reference.

FIELD OF THE INVENTION

The present description refers to heart valve prostheses, both of the biological and of the mechanical type including a prosthetic valve annulus defining an orifice for the passage of blood flow and at least one prosthetic valve leaflet member configured for regulating the blood flow through said prosthetic valve annulus.

BACKGROUND

Cardiac valve insufficiency is a pathology that generally leads to a surgical intervention for the replacement of the diseased native heart valve. In the field of heart valve surgery both biological and mechanical prostheses are known, the former being generally made from portions of biological tissue (for example bovine pericardium), the latter being made e.g. either of metal materials, polymeric materials or composite materials, possibly clad with a biocompatible coating (i.e. pyrolitic carbon).

In a large majority of cases, a diseased native heart valve is found to allow a blood regurgitation through the leaflets, whereby a fraction of the blood flow which is actively (i.e. by a positive action) displaced by the pulsating heart leaks through the diseased valve in a direction opposite to that normally intended for the passage of blood flow due to sub-optimal coaptation of the valve leaflets.

Taking a diseased native heart valve as example, it is known that when the mitral valve is regurgitating a progressive decrease in left ventricle afterload (due to low pressure backward blood flow) and volume overload (i.e. high preload due to the regurgitated blood volume) occurs. This results, i.a. in a variation of the enzymatic myocytes equipment and of the pattern of actine-myosine cross bridge.

In other words, the entire heart cycle is affected, because the left ventricle experiences a lower blood pressure when ejecting blood through the aortic valve during systole due to the blood leak through the diseased mitral valve.

Additionally, when admitting blood into the left ventricle (diastole) via the mitral valve from the pulmonary veins, the left ventricle experiences a higher than normal preload due to the additional volume of blood that had previously leaked through the diseased valve due to the regurgitation and that now flows back in.

When a diseased mitral valve is replaced, the left ventricle experiences a sudden increase in afterload and a simultaneous decrease in preload. The first effect is due to the replacement mitral valve (i.e. prosthetic) being designed not to allow any blood leak (regurgitation) therethrough, so that when ejecting blood through the aortic valve during systole, the left ventricle experiences a higher blood pressure than that experienced with the diseased mitral heart valve because no blood leak occurs through the prosthetic mitral valve.

The second effect is due to the substantial absence of the regurgitated blood volume in the left ventricle during diastole.

A preload/afterload mismatch therefore occurs, which may lead to a left ventricle failure. Additionally, myocardial oxygen needs may increase as a consequence of a higher energy demand.

This furthermore may result in an intractable cardiogenic shock. In this situation the recovery sometimes requires several days of inotropic support.

OBJECT AND SUMMARY

It is therefore an object of the invention that of improving the post-operative recovery after a valve replacement surgical intervention.

The above object is achieved by a prosthetic heart valve having the features of one or more of the claims that follow. The claims form an integral part of the technical disclosure herein provided in relation to the invention.

More particularly, the object is achieved by a prosthetic heart valve including:
  a prosthetic valve annulus defining an orifice for the passage of blood flow,
  at least one prosthetic valve leaflet member including at least one coaptation surface configured for cooperating with at least one corresponding coaptation surface of said prosthetic heart valve to regulate blood flow through said orifice, said at least one valve leaflet member being displaceable by the blood flow between a closed position and an open position to produce, correspondingly, a contact and a separation of cooperating coaptation surfaces,
wherein in the open position the separation of the cooperating coaptation surfaces enables the blood flow through said orifice in a first direction, and
wherein in the closed position the contact of the cooperating coaptation surfaces prevents the blood flow through said orifice in a second direction, opposite to said first direction,
wherein the prosthetic heart valve includes at least one device configured for preventing at least in part the contact between cooperating coaptation surfaces, so that a blood regurgitation in said second direction is enabled, and wherein said at least one device is configured for ceasing its action after a predetermined amount of time.

BRIEF DESCRIPTION OF THE FIGURES

Various embodiments of the invention will now be described with reference to the attached figures, provided purely by way of non limiting example, and wherein:

FIG. 1 is a sectional, schematic, view of heart valve prosthesis according to various embodiments in a first operating condition, FIG. 2 is a view according to the arrow II of FIG. 1, FIG. 3 is a sectional, schematic, view corresponding to that of FIG. 1 but showing the valve prosthesis in a second operating configuration, FIG. 4 is a view according to arrow IV of FIG. 3, FIG. 5 is a partly sectioned, schematic, view of a detail indicated by the arrow V in FIG. 1, FIG. 6 is a sectional view according to the line VI-VI of FIG. 5 and showing a first condition, FIG. 6A is an enlarged sectional view of FIG. 6, FIG. 6B is a partial view according to the arrow VI/B of FIG. 6A, FIG. 6C is a partial view of a detail of FIG. 6A, sectioned along the line VI/C-VI/C of FIG. 6A FIG. 7 is a sectional view corresponding to that of FIG. 6 and showing another condition, FIG. 10 is a schematic view of detail according to the arrow X of FIG. 1, FIG. 11 is a sectional, schematic, view according to the line XI-XI of FIG. 10, FIG. 12 is a perspective, schematic, view of a prosthetic heart valve according to further embodiments of the invention, FIGS. 13 and 14 are views according to the arrow XIII of FIG. 12 and showing two different operating conditions, FIG. 15 illustrate a heart valve prosthesis according to further embodiments.

DETAILED DESCRIPTION OF PREFERRED EMBODIMENTS

Figure 8:
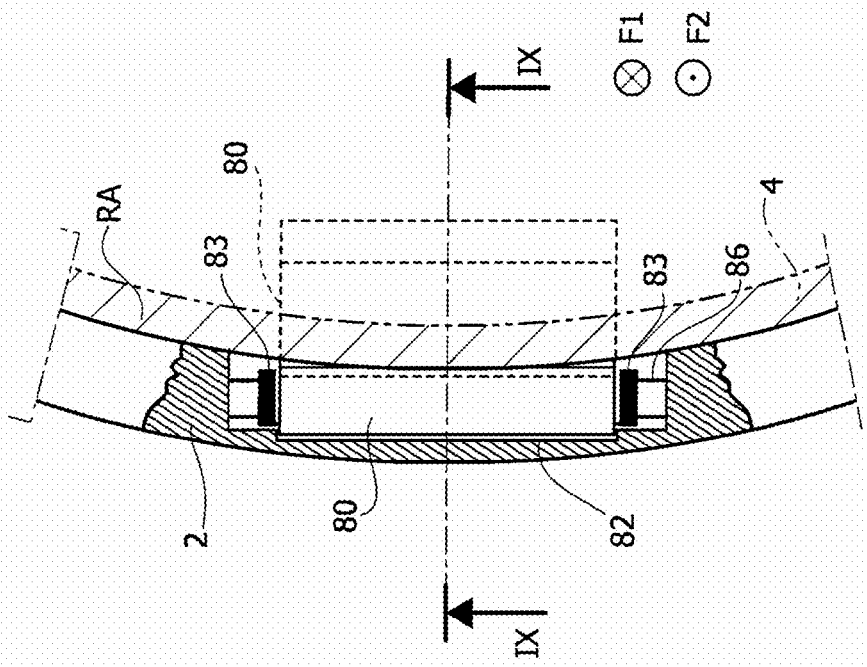
FIG. 8 is a partly sectioned, schematic, view corresponding to that of FIG. 5 but according to further embodiments of the invention.

In the following description, numerous specific details are given to provide a thorough understanding of embodiments. The embodiments can be practiced without one or more of the specific details, or with other methods, components, materials, etc. In other instances, well-known structures, materials, or operations are not shown or described in detail to avoid obscuring aspects of the embodiments.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The headings provided herein are for convenience only and do not interpret the scope or meaning of the embodiments.

In FIGS. 1 and 3 the reference number 1 identifies as a whole a heart valve prosthesis according to various embodiments and of the mechanical type.

The heart valve prosthesis 1 includes a prosthetic valve annulus 2 which in various embodiments may be a ring member having a wall thickness t and to which at least one prosthetic valve leaflet member 4 is movably connected. By the term "movably connected" it is meant to indicate the presence of a coupling that allows a movement of the leaflet along at least one degree of freedom to simulate the behaviour of a native valve leaflet. Furthermore, the term "leaflet member" as used herein is intended to cover any device or component that is capable of providing an action aimed at reproducing that of a native valve leaflet.

Examples of such components/devices may include "mechanical" prosthetic valve leaflets (i.e. intended to be applied on mechanical heart valve prostheses), "biological" prosthetic valve leaflets (i.e. made of biological tissue) and also ball members of mechanical "ball valve" prostheses, which are capable of regulating the blood flow as well as any other previously mentioned device.

For this reason, and for the sake of conciseness, the generic term "leaflet" will be primarily used herein, such term being intended to encompass, where applicable, one or more of the devices/components mentioned above.

In various embodiments the at least one prosthetic valve leaflet includes at least one coaptation surface configured for cooperating with at least one corresponding coaptation surface of the prosthetic heart valve to regulate blood flow through the orifice defined by the prosthetic valve annulus 2. In some embodiments, a first coaptation surface may be provided on the edge of the leaflet 4 and a second coaptation surface may be provided by the prosthetic valve annulus 2 itself (for example in tilting disc prosthetic heart valves).

In other embodiments, such as those shown in FIGS. 1 to 4, the prosthetic heart valve 1 includes two leaflets 4 pivotable around respective axes X1, X2 (orthogonal to a main axis Z1 of the heart valve prosthesis and of the prosthetic valve annulus 2), generally D-shaped and each including first coaptation surfaces C1, C2, C3, C4 which are configured for cooperating with corresponding second coaptation surfaces C5, C6 provided on the valve annulus 2, as well as with a corresponding coaptation surface C1 of the other leaflet 4 (see below for details).

In particular, in various embodiments:

the coaptation surface C1 is provided in correspondence of a straight portion of the "D" shape of each leaflet and it is configured for cooperating with the corresponding coaptation surface C1 on the other valve leaflet;

the coaptation surface C2 is provided at the curved portion of the "D" shape and it is configured for cooperating with a corresponding coaptation surface C5 on the inner surface of the prosthetic valve annulus 2, the coaptation surfaces C3, C4 are provided at parallel rectilinear portions of the "D" shape orthogonal to the straight portion whereat the surface C1 is provided, and are located on opposite sides with respect to the surface C1; the coaptation surfaces C3, C4 are configured for cooperating with corresponding coaptation surfaces C6 on the prosthetic valve annulus 2.

Generally, it may be said that in various embodiments each leaflet includes at least one coaptation surface which is adapted to cooperate with another coaptation surface which is provided on the valve, this meaning that the second coaptation surface may be located either on another leaflet or on the prosthetic valve annulus or both.

In various embodiments, the prosthetic heart valve 1 includes one or more devices configured for influencing the contact between the cooperating coaptation surfaces when the leaflets are displaced towards a closed position.

With specific reference to FIGS. 1 to 4, a schematic representation of two such devices is indicated respectively with reference numbers 8, 10. Note that in the figures shown herein both the devices 8, 10 are depicted, but in various embodiments it is envisaged that only one of the devices 8 or 10 be provided. Furthermore, in the examples shown in the figures, the devices 8, 10 are provided in pairs, namely there is at least one device 8, 10 operatively associated to each leaflet 4, but embodiments are also possible wherein one and only device 8, 10 is provided and operatively associated to one leaflet only.

However, in some embodiments both the devices 8, 10 may be present.

In various embodiments, the device 8 is a peripheral device, configured for exerting its action at the prosthetic valve annulus, while the device 10 is a leaflet device, i.e. configured for exerting its action at the prosthetic valve leaflets.

Generally, the action of such devices 8, 10 is aimed at preventing the complete closure of the heart valve prosthesis so to allow a temporary regurgitation of blood through the valve prosthesis itself. Furthermore, as will be detailed in the following, such devices are configured for ceasing their action after a predetermined amount of time in order to restore the full performances of the heart valve prosthesis.

In various embodiments, each device 8, 10 is configured for preventing at least in part the contact between cooperating coaptation surfaces, so to enable a blood regurgitation through the prosthesis 1.

In the embodiments depicted in FIGS. 1 to 4, the peripheral device 8 may be located on the surface C5 (i.e. on the valve annulus 2) and it is configured for contacting the valve leaflet 4 in order to avoid the contact between the coaptation surfaces C2, C5 at at least a portion of the respective contact areas. In other embodiments it may be envisaged to have the device 8 applied to the valve leaflet 4 (i.e. applied to the coaptation surface C2). Note that the at least partial lack of contact created between the surfaces C5 and C2 also leads to the lack of contact (at least in part) of other cooperating coaptation surfaces, namely the surfaces C1 on the edge of the leaflets 4 and the surfaces C3, C4 and C6.

In such embodiments it is preferable that the device 8 be sized and dimensioned so to prevent at least in part the contact between a pair of cooperating coaptation surfaces without contacting directly the coaptation surface on which it is not applied.

This in order to prevent the leaflets from being locked in the closed position. In fact, it is not unlikely that in case the device 8 were to contact both the cooperating coaptation surfaces, the device 8 would—in the closed position of the leaflets 4—be "squeezed" between the leaflet 4 itself and the annulus 2, thereby creating an interference fit of the former into the latter. This mainly because the closure forces acting on the valve leaflets are typically higher than the opening forces.

The second device 10 may be positioned at the coaptation surface C1 of each valve leaflet.

In various embodiments, each device 8, 10 may be in the form of a web, a wedge, a tab, a patch, a relief, a shim or a film, or any possible equivalent.

In one embodiment, including only two peripheral devices 8, each device 8 is a 0.6 mm thick patches. In another embodiment, including only two leaflet devices 10 (each associated to a respective prosthetic valve leaflet 4), each device 10 is a 0.2 mm thick patch or film. In both cases, a regurgitation area of approximately 25 mm$^2$ can be obtained.

As previously set forth, each device 8, 10 is configured for allowing a temporary blood regurgitation through the prosthetic heart valve 1. Further details are provided below.

As well known, the prosthetic valve leaflets 4 are displaceable by the blood flow between a closed position (shown in FIGS. 3 and 4) and an open position (shown in FIGS. 1 and 2) to produce, correspondingly, a contact and a separation of the cooperating coaptation surfaces.

In the open position of the prosthetic valve leaflets (this applies regardless of the number of the valve leaflets, i.e. when there is only one valve leaflet or more than two) the separation of the cooperating coaptation surfaces (in these embodiments C1, C2, C3, C4, C5, C6—see above for details about the coaptation—) enables the blood flow through the orifice in a first direction F1.

In the closed position the contact of the prosthetic valve leaflets 4 the contact of the cooperating coaptation surfaces (in these embodiments C1, C2, C3, C4, C5, C6—see above for details about the coaptation—) prevents the blood flow through the orifice in a second direction F2, opposite to the first direction F1.

In various embodiments, each device 8, 10 is configured for preventing at least in part the contact between the first and second cooperating coaptation in order to prevent a complete closure of the valve leaflet(s) and enable thereby a blood regurgitation in the second direction F2.

Furthermore, in various embodiments the devices 8, 10 are made at least in part of bio-degradable and/or bio-resorbable material, i.e. a material which is capable of disappearing after a pre-determined amount of time, for example due to the erosion action conveyed by the blood flow. In this way, the action of the devices 8, 10 may cease after such a pre-determined amount of time.

Examples of bio-degradable/bio-resorbable materials which may be used for the devices 8, 10 may include bio-resorbable polymer gels such as 3-hydroxypropionic acid, polyylactic (L, DL) acid, poly caprolactone, poly glycolide, poly lactic co-glycolide, poly dioxanone, polytrimethyl carbonate, ε-polylysine, hyaluronic acid, poly saccharides. Additionally, bioresorbable magnesium alloys may also be used, for example in embodiments such as those shown in FIGS. 10-11.

In various embodiments the bio-degradable/bio-resorbable material may be chosen so to exhibit a full degradation in 3 to 6 weeks for example by surface or bulk erosion, or even by poor elasticity.

Generally it is preferable that the bio-degradable/bio-resorbable material have a sufficient diffusion in the blood flow, and the diffusing area and diffusibility of the bio-degradable/bio-resorbable material are chosen accordingly.

In other embodiments, the bio-degradable/bio-resorbable material may be chosen among gels which exhibit a full degradation in 3-6 weeks by surface erosion only. Preferably the gel should exhibit high resistance to pressure, small elasticity and high adhesivity on carbon, in order to achieve a sufficiently strong connection with a bio-compatible coating possibly applied to the prosthetic heart valve 1.

In other embodiments, a polymer gel which exhibits full degradation in 3 to 5 weeks by surface erosion only may be chosen, and preferably a gel exhibiting high adhesivity on tissues is chosen.

Thanks to the presence of the devices 8 or 10 the alteration of the preload and the afterload of the left ventricle, in case the prosthetic valve 1 is used for mitral valve repair, may be consistently reduced.

In particular, after diastole—wherein a blood flow to the left ventricle is enabled by the valve leaflets 4 in the open position as shown in FIGS. 3, 4—the complete closure of the valve leaflets 4 is prevented by the devices 8, 10.

Note in this respect the outline of each valve leaflet 4 in dashed line which provides evidence of the position of the regurgitation area RA resulting from the lack of contact in correspondence of at least a portion of the coaptation surfaces at (and near) the location of the devices 8, 10.

In this way, still with reference to a mitral valve repair, during systole a blood back flow to the left atrium is enabled through the regurgitation area RA so that the behaviour of the newly implanted heart valve prosthesis 1 resembles that of the diseased native heart valve.

In the diastole that follows the regurgitated blood volume enters the left ventricle, thereby resembling the behaviour of the diseased native heart valve. So to say, thanks to the prosthetic heart valve 1 according to the embodiments herein described, the heart perceives only slight changes with the respect to the operation with the diseased native heart valve, which helps in minimizing the negative impact of the valve repair intervention on the patient.

As time passes by the volume of the devices 8 or 10 is progressively reduced due to erosion and/or degradation caused, for example, by the blood flow which impinges thereupon.

This gradually leads to the increase of the contact area between cooperating first and second coaptation surfaces, thereby reducing as a consequence the regurgitation area RA.

In this way the pre-load (i.e. the end-diastolic volume) is gradually decreased to normal values while the afterload is gradually increased because the blood leaks through the regurgitation area RA during systole get progressively smaller.

When the devices 8 or 10 have been eroded to such an extent that they cease their action (either because they are completely disappeared, or, as will be described in the following, because a positional and volumetric variation occurred) the full contact area between the cooperating coaptation surfaces of the valve leaflets and the prosthetic valve annulus 2, 4 is restored, thereby enabling the prosthetic heart valve 1 to function according to design specifications.

With reference to FIGS. 5 to 7, further embodiments of the device 8 are shown in enlarged views. In such embodiments, the device 8 may take the form of a hollow cylindrical sector housed in a local enlargement 20 of the wall thickness t of the prosthetic valve annulus 2, wherein the enlargement 20 preferably protrudes in radial direction outwards of the annulus 2 for the passage of blood flow. In some embodiments the local enlargement may be 1.8 mm (including the wall thickness t, which in various embodiments is equal to 1 mm).

In various embodiments the device 8 may include a first portion 80 made of substantially rigid, non bioresorbable/non-biodegradable material which is into contact with (in some embodiments attached to) a second portion 81 which in various embodiments is made of a bio-resorbable/biodegradable material, e.g. a bioresorbable gel or a bioresorbable polymer. In other embodiments, the biodegradable material used for the portion 81 may be more rigid than a polymer gel (e.g. a a bioresorbable magnesium alloy can be used) so that it can offer a higher resistance to external action but anyway the portion 81 shall be made of biodegradable material.

Within the local enlargement 20 there may be provided guide walls 82 which are configured for guiding the portion 80 in a sliding movement therethrough.

Thanks to the presence of the guide walls 82 the portion 80 can thus slide inwards and (theoretically) outwards of the prosthetic valve annulus 2, in a way which will be described in the following.

Guide walls 82 define a cavity 820 which in various embodiments is filled partly by the portion 81

In various embodiments The first portion 80 is in part housed within the cavity 820 in the volume not occupied by the portion 81, and in part (preferably a larger part) it protrudes out of the cavity defined by the guide walls 82 and inwards of the orifice for the passage of blood flow, as shown in FIG. 6.

This corresponds to the condition (shown in FIG. 6) of the device 8 on a new, ready to be implanted prosthetic heart valve (and even a newly implanted one, in the very first stint of its service life). In other words, when the second portion 81 has a maximum volume (corresponding to the beginning of service life), the first portion 80 of the hollow cylindrical sector protrudes outwards of the cavity 820 and radially inwards of the orifice of the heart valve prosthesis 1 by a maximum extent, so that the regurgitation area created thereby is also at a maximum value.

In this condition, at least a leading edge 800 of the portion 80 contacts a surface of the valve leaflet 4, thereby preventing at least in part the contact of the coaptation surfaces C2, C5. The contact between other cooperating coaptation surfaces (e.g. C3, C4 and C6) will be accordingly affected, taking into consideration the geometry of the valve leaflet 4.

In various embodiments, the portion 80 may be biased inwards into the cavity 820 and against the portion 81 by an elastic biasing element 83 which may take the form of a torsion wire or a helical spring wound with a small diameter. In various embodiments the elastic biasing element 83 may be made of steel or titanium alloy or even a shape memory material such as Nitinol.

In such embodiments, the elastic biasing element 83 may include a wire like element helically wound and having a first end 84 which is connected to the prosthetic valve annulus 2 and a second end 85 which is connected to the portion 80.

In some embodiments, in order to facilitate the positioning of the elastic biasing element 83, a miniaturised pin 86 may be provided within the prosthetic valve annulus 2 at the local enlargement 20 so that it provides both a position reference and a support to the elastic biasing elements 83.

In various embodiments only one elastic biasing element 83 is provided for each device 8. In other embodiments, such as those shown in FIG. 5, a pair of elastic biasing elements 83 is arranged on opposite sides of the hollow cylindrical device 8.

After the implantation of the heart valve prosthesis, the blood flow that impinges upon the heart valve prosthesis 1 and in particular on the prosthetic valve annulus 2 gradually erodes the biodegradable/bioresorbable material of which the portion 81 is made. Blood may penetrate through the clearance between the portion 80 and the guide walls 82, so that it can reach the portion 81.

In greater detail, in one embodiment a biodegradable gel is chosen as a biodegradable/bioresorbable material. The biodegradable gel fills the empty space corresponding to the portion 81 and the clearance S between the portion 80 and the guide walls 82 (see FIGS. 6A-6C), which prolongs the portion 81.

The contact area (at which erosion occurs) between the blood stream and the biodegradable gel corresponds—so to say—to a cross section of the clearance S, i.e. it has substantially the shape of a rectangular frame surrounding the portion 80.

When the recoil mechanism of the portion 80 (e.g. the elastic biasing element 83) exerts its action on the portion 80 itself, pressure is applied on the gel of the portion 81, so that any eroded volume of gel at the interface with the blood stream promotes a roll-in movement of the portion 80 resulting in an "extrusion" of the portion 81 of the same volume through the clearance S.

At the same time, the action of the elastic biasing element 83 pushes the portion 80 back into the cavity 820, and gradually reduces the extent by which the portion 80 protrudes radially inwards of the prosthetic valve annulus 2.

As the portion 80 is gradually rolled back into the cavity between the walls 82, the coaptation surfaces C2, C5 get into contact with one another at a progressively larger area when the valve leaflets 4 are brought in the closed position (the same goes, accordingly, with the other affected cooperating coaptation surfaces), and the regurgitation area RA is reduced accordingly.

When the portion 80 is completely housed in the valve annulus 2, the residual volume of gel is equal to that of the clearance "S" (i.e. contact area multiplied by extension of the clearance).

In this situation, the position of the portion 80 is maintained fixed by the guide walls 82 (in particular that at the bottom of the cavity 820), so that any action possibly exerted by the elastic biasing element 83 results in no displacement of the portion 80, therefore no further extrusion of the gel will occur. The residual volume of gel will be trapped in the clearance S and the area in contact with the blood flow will clot and then will be filled by fibrosis.

FIG. 7 shows the condition of the device 8 after the portion 81 has been completely eroded by the blood flow. The portion 80 is completely retracted inside the valve annulus 2, in particular inside the local enlargement 20, and it is held in position by the action of the elastic biasing element 83.

Note that in various embodiments the angular extension of the portion 80 of the device 8 is chosen so that, when the device 8 is completely retracted inside the cavity 820, the leading surface thereof lies flush with or slightly below the inner cylindrical wall of the prosthetic valve annulus 2. This in order not to impede the complete and optimal contact between the coaptation surfaces C2, C5 and in order not to disturb the blood flow when the leaflets 4 are in the open position.

In some embodiments the final position (i.e. that shown in FIG. 7) of the portion 80 may be locked by the combined action of the biasing element 83 and a pawl member (not shown) in order to ensure that no undesired displacement (rollout) of the portion 80 will occur.

Figure 9:
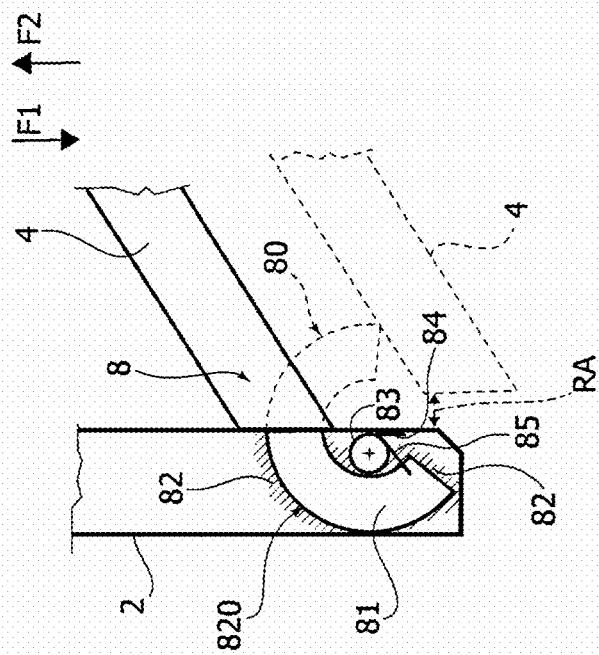
FIG. 9 is a sectional view according to the line IX-IX of FIG. 8.

With references to FIGS. 8, 9, a variant of the embodiments depicted in FIGS. 5 to 7 is shown in enlarged scale. The difference resides primarily in the smaller dimensions of the peripheral device 8, because in such embodiments the device 8 is housed completely within the wall thickness t of the annulus 2, without any local enlargement thereof.

The operation of the peripheral device 8 is exactly the same as described with reference to FIGS. 5 to 7 and the reference numbers, where identical to those previously used, denote the same components.

In other embodiments, the torsion wire 83 may be substituted by a miniaturized, remotely controlled actuator configured for rolling the peripheral device 8 back into the cavity 820, so that the action of the device 8 may cease after a predetermined amount of time.

With reference to FIGS. 10, 11, an enlarged view of the second device (leaflet device) 10 is provided herein. In various embodiments the leaflet device 10 may take the form of a film of bio-degradable/bio-resorbable material applied on a portion of the coaptation surfaces C1 of the leaflets 4. In various embodiments, such a film may extend over the entire area of the coaptation surfaces C1, while in other embodiments the film 10 may extend only for part of the length (in the direction of the axes X1, X2) of the valve leaflets 4 and/or only for part of the thickness of the valve leaflets 4.

Whatever form and extension the device 10 may be given, the action thereof prevents at least in part the contact of coaptation surfaces C1 of the valve leaflets 4 (i.e. at least a portion of the contact area thereof), so that a regurgitation area RA is created between the leaflets 4 (see FIG. 10). Of course, due to the geometry and the arrangement of the leaflets 4, the lack of contact between the coaptation surfaces C1 also results in a lack of contact at one or more locations of the cooperating coaptation surfaces C2, C5 and C3-C4, C6.

Generalizing, regardless of the provision of a peripheral or a leaflet device 8, 10, a regurgitation area RA will be created both between the leaflets 4 and between the leaflets and the annulus 2.

In various embodiments, a contact occurs directly between the devices 10 on each leaflet 4: in this case the risk of having the leaflets locked in the closed position is quite lower than that affecting the peripheral devices 8 because, due to the position of the axes X1, X2 (closer to the main axis Z1 of the valve prosthesis 1) the opening forces have a more favourable lever ratio. To this end, it is however preferable that the bio-degradable/bio-resorbable material of the device 10 be chosen so that separate pieces thereof (e.g. those of the two leaflet devices 10) do not exhibit reciprocal adhesion properties.

In further embodiments both the devices 8, 10 may be present and they may be exploited for example in such manner.

The materials of each device may be chosen so to erode over different time spans. The device made of the material with the longer degradation time may be undersized with respect to the dimensions it should have if it were to be the sole device, so that it does not come into play in the first moments of the prosthesis service life.

The other device, made of a material which exhibits a shorter degradation time, may be sized normally, so that it does comes into play at the very beginning of the service life of the prosthesis.

It may happen that, due to the geometry of the device and/or the location at which the device is positioned and/or the characteristics of the blood flow, the effectiveness thereof may significantly decrease well before the complete erosion thereof has occurred.

Therefore, when both the peripheral and the leaflet device are present, that which is expected to lose its effectiveness in a shorter time, if it were the sole device, may be designed to be eroded in a shorter time. In this way when effectiveness is almost lost (i.e much lower regurgitation area than that considered when designing the prosthesis), the second device—previously inactive due to its undersizing—may come into play and restore the effectiveness.

Additionally, by doing so one may also—so to say— "program" a non linear change in the regurgitating flow evolution.

With reference to FIGS. 12 to 14, a heart valve prosthesis according to further embodiments is shown herein and indicated by the reference 100.

In such embodiments, the heart valve prosthesis 100 is a biological prosthetic heart valve including a prosthetic valve annulus 200 and a plurality of biological valve leaflets 400. In the embodiments shown herein the heart valve prosthesis 100 may be suitable for replacement of aortic or tricuspid valve. With reference to FIGS. 13 and 14, each leaflet 400 includes a leading edge 402 whereat a coaptation surfaces C100 is provided.

When implanted, the blood flow opens and closes the valve leaflets 400 of the prosthesis 100, so that when the leaflets 400 are in the open position as shown in FIG. 13 the separation between the cooperating coaptation surfaces C100 enables the blood flow through the orifice defined by the annulus 200 in the direction F1, and when the leaflets 400 are in the closed position shown in FIG. 14 the contact of the cooperating coaptation surfaces C100 prevents the blood flow through the orifice in the direction F2, opposite to F1.

In various embodiments the prosthesis 100 may include a plurality of devices 110 located on the coaptation surfaces C100 at a position proximate to commissures C whereat the valve leaflets re-join. The devices 110 are configured for allowing a blood regurgitation through the prosthesis 100 by preventing at least in part the contact between the coaptation surfaces C100 (i.e. in correspondence of least a portion of the contact area thereof).

Each device 110 in various embodiments may be in the form of a web, a wedge, a tab, a patch, a relief, a shim or a film, made of bio-degradable/bio-resorbable material, e.g. a gel applied (e.g. coated) on the valve leaflets 400.

When the leaflets 400 are in a closed position, as shown in FIG. 14, the contact of the coaptation surfaces 100 is prevented at a location proximate to the commissures C, therefore the regurgitation area is concentrated primarily at the commissures C.

As in the embodiments previously described, the devices 100 are progressively eroded by the blood flow impinging thereupon so that the regurgitation area is gradually reduced to zero.

That is, when the prosthesis 100 is used for example in a tricuspid valve replacement intervention, the preload/afterload of the right ventricle may be initially kept at values corresponding to those of the diseased native heart valve.

During systole, a fraction of the blood intended to be ejected through the pulmonary vein leaks through the regurgitating prosthetic valve 100. During diastole, the regurgitated volume is again admitted into the ventricle together with the diastolic volume, thereby resembling the behaviour of the diseased native heart valve. However the behaviour of the prosthetic heart valve 100 gradually evolves towards a nominal one i.e. according to the design specifications, which allows for a gradual recovery of the heart after the valve replacement intervention.

Without prejudice to the underlying principles of the invention, the details and the embodiments may vary, even significantly, with respect to what has been described herein, purely by way of non limiting example, without departing from the scope of the invention as defined by the annexed claims. Furthermore, various modifications and additions can be made to the exemplary embodiments discussed without departing from the scope of the invention.

For example, the prosthetic valve according to the embodiments of the invention is not limited to a mitral or a tricuspid valve, as the foregoing disclosure applies to any prosthetic heart valve, regardless of the type, and the material of the prosthetic heart valve, and also regardless of the number and arrangement of the prosthetic valve leaflets.

Figure 15:
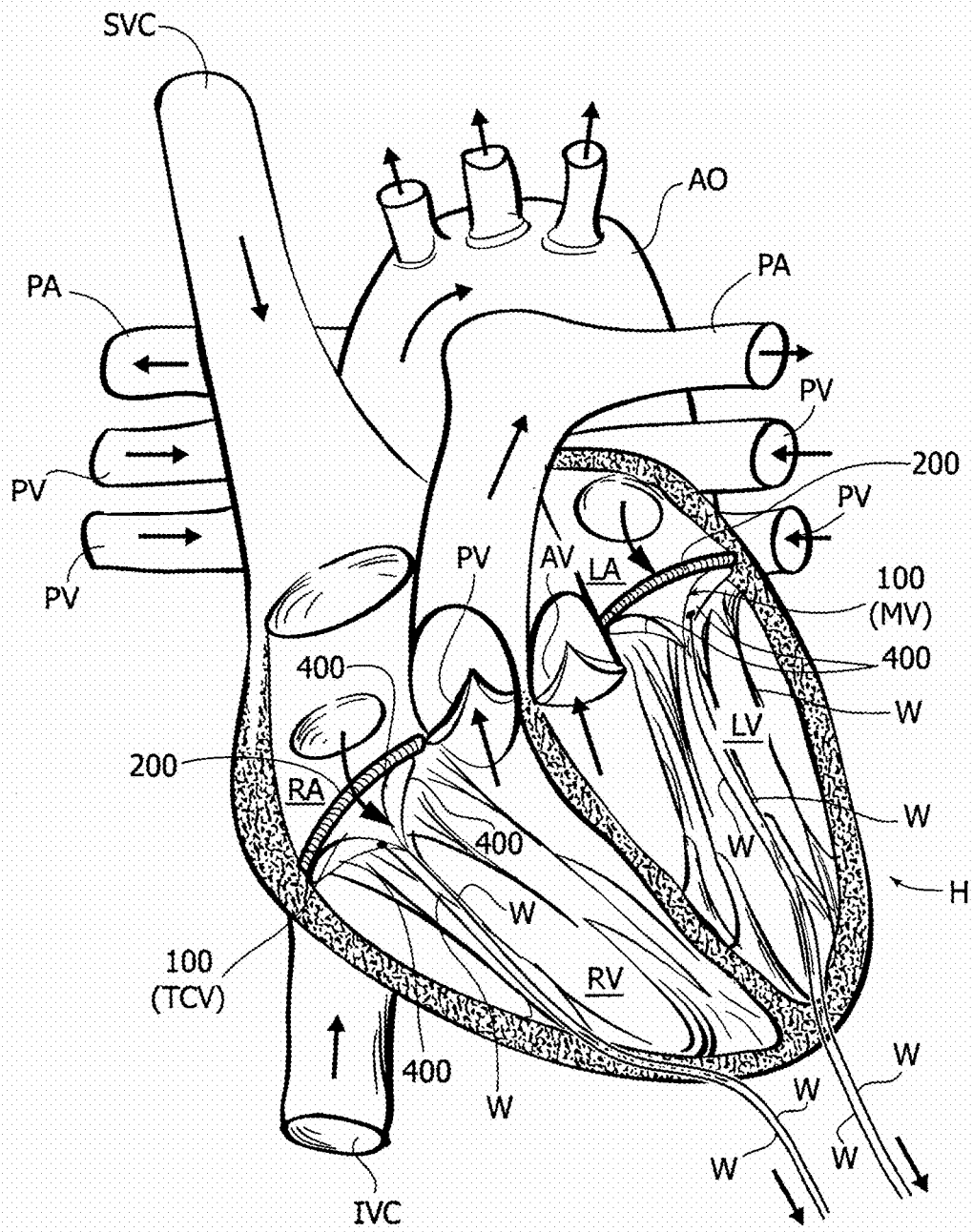
Figure 16:
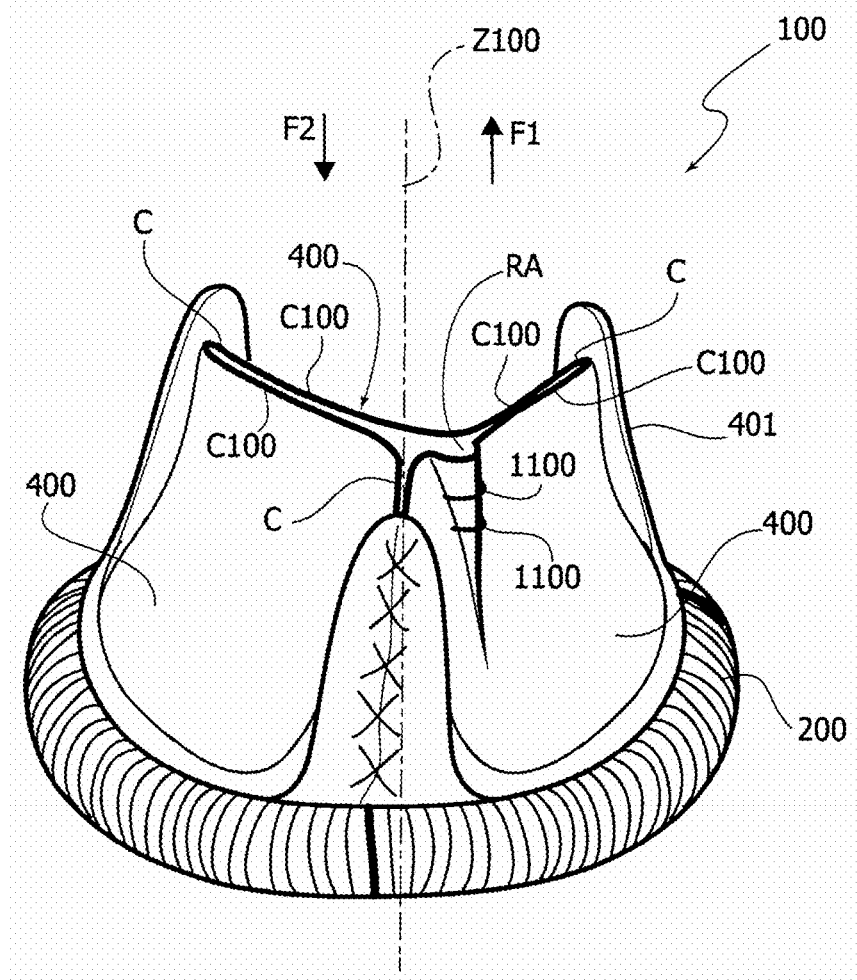
FIG. 16 illustrates a heart valve prosthesis according to yet further embodiments.

Additionally, in yet further embodiments of the invention, such as those of FIGS. 15-16, other types of devices configured for altering the coaptation of the valve leaflets are envisaged.

In FIG. 15 a schematic view of a human heart H is provided. The main blood vessels are labeled for prompt reference (the direction of blood flow are also shown). Such vessels include the aorta AO, the pulmonary veins PV, the pulmonary artery PA, the inferior vena cava IVC and the superior vena cava SVC. The natural heart valves schematically depicted in FIG. 15 include the pulmonary valve PV, the tricuspid valve TCV, the mitral valve MV and the aortic valve AV.

The right atrium and the left atrium are indicated by RA and LA respectively, while the right ventricle and the left ventricle are indicated by RV and LV, respectively.

In FIG. 15 the references associated to the tricuspid valve TCV and the mitral valve MV are provided in parenthesis in order to indicate that the heart valve prosthesis 100 may replace one of them (at least). A pair of heart valve prostheses 100 are displayed in FIG. 15 just for the ease of description, without any limiting meaning.

Instead of the devices 8, 10 described in the foregoing, the heart valve prosthesis 100 may be provided with a thread W which is routed so to form a loop at one of the prosthetic valve leaflet 400 (i.e. the latter is pierced by the thread W). After the intervention, the thread may be routed through a papillary muscle, the through the wall of the heart (for example at or near the apex) and then it may be routed through the thorax of the patient in the same way as post-operative electrodes, the thread may then be slightly tensioned in order to produce a small deformation of the valve leaflet 400 which in turn prevents at least in part the contact between cooperating coaptation surfaces C100 of the leaflets 400. The action of the thread W may then cease either by manual removal thereof or by erosion. In the first case, in various embodiments no knot is provided on the thread W, so that removal of the thread W may occur by simply pulling the wire from outside the body of the patient (additionally, in this way either end may be used to pull the thread). In the second case the thread W shall be made of biodegradable/bioresorbable material, so that it will be eroded by the blood flow. Additionally, a subsequent manual removal of the portions of the thread W not eroded by blood flow may occur e.g. by pulling the two ends of the thread from outside. However, the manual removal of the thread may turn out to be necessary essentially when a non-biodegradable/non-bioresorbable thread is used, because generally a biodegradable/bioresorbable thread experiences full degradation (therefore completely disappearing) even in the absence of direct impingement by the blood flow.

Furthermore, the inventor also observed that the above method for altering the coaptation of the leaflets 400 by using the thread W may be performed on a native, in particular repaired, heart valve.

With reference to FIG. 16, the heart valve prosthesis 100 is shown having a device for altering the coaptation of the valve leaflets, in particular configured for preventing at least in part the contact between cooperating coaptation surfaces thereof, according to yet further embodiments. In such embodiments the device is a leaflet device 1100 in the form of a biodegradable/bioresorbable stitch that creates a local deformation of one or more valve leaflets 400, in a manner that resembles at least in part the action of a purse string. The stitch 1100 creates a defect in the leafet coaptation by forcing a portion of the valve leaflet to bulge outwards (for example, in other embodiments it may be envisaged that the leaflet be bulged inwards), thereby creating a small regurgitation area RA. After a predetermined amount of time the stitch(es) 1100 is (are) eroded (e.g. resorbed) by the blood flow, so that the prosthetic heart valve 100 may start to function according to design specifications, i.e. allowing substantially no blood regurgitation.

In view of the foregoing it follows that there are envisaged both embodiments wherein the at least one device configured for altering the coaptation of the valve leaflets, in particular configured for preventing at least in part the contact between cooperating coaptation surfaces thereof, ceases its action by removal thereof (see for example FIG. 15), and embodiments wherein such device ceases its action by erosion (see the embodiments wherein the at least one device is made—at least in part—of biodegradable/bioresorbable material).

The invention claimed is:

1. A prosthetic heart valve including:
a prosthetic valve annulus defining an orifice for the passage of blood flow,
at least one prosthetic valve leaflet member including at least one coaptation surface configured for cooperating with at least one corresponding coaptation surface of said prosthetic heart valve to regulate blood flow through said orifice, said at least one prosthetic valve leaflet member being displaceable by the blood flow between a closed position and an open position to produce, correspondingly, a contact and a separation of cooperating coaptation surfaces,
wherein in the open position the separation of the cooperating coaptation surfaces enables the blood flow through said orifice in a first direction,
wherein in the closed position the contact of the cooperating coaptation surfaces prevents the blood flow through said orifice in a second direction, opposite to said first direction, and
at least one device configured for preventing at least in part the contact between cooperating coaptation surfaces, so that a blood regurgitation in said second direction is enabled, and in that said at least one device is configured for ceasing its action after a predetermined amount of time,
a ring member defining said prosthetic valve annulus;
two leaflets of said at least one prosthetic valve leaflet member movably connected to said ring member;
said at least one device operatively associated to each leaflet of said two leaflets, said at least one device comprising a peripheral device operatively associated to each leaflet of the two leaflets and applied to the ring member, said peripheral device being configured for preventing at least in part the contact between at least one coaptation surface of the ring member and a corresponding coaptation surface of a leaflet of the two leaflets,
wherein the peripheral device includes a hollow cylindrical sector comprising a first portion made of a non-biodegradable or non-bioresorbable material and a second portion made of a bio-degradable or bio-resorbable material, wherein said first portion is guided into a cavity defined by guide walls provided within said ring member.

2. The heart valve prosthesis of claim 1, wherein said at least one device is configured for ceasing its action by erosion thereof.

3. The heart valve prosthesis according to claim 1, wherein said at least one device includes a leaflet device located at cooperating coaptation surfaces of each leaflet, said leaflet device being configured for preventing at least in part the contact between the cooperating coaptation surfaces of said leaflets.

4. The heart valve prosthesis according to claim 1, wherein when the second portion of the hollow cylindrical sector has a maximum volume, the first portion of the hollow cylindrical sector protrudes outwards of said cavity and radially inwards of the orifice of the heart valve prosthesis by a maximum extent, said second portion further extending in a clearance between said first portion and the guide walls.

5. The heart valve prosthesis according to claim 4, wherein the first portion of the hollow cylindrical sector is biased elastically towards the interior of said cavity.

6. The heart valve prosthesis according to claim 1, wherein said peripheral device is housed within a wall thickness of said ring member.

7. The heart valve prosthesis according to claim 1, wherein said peripheral device is housed in a local enlargement of a wall thickness of the ring member, said local enlargement protruding radially outwards from said ring member.

8. The heart valve prosthesis of claim 1 further comprising a plurality of coapting valve leaflets made of biological material.

9. The heart valve prosthesis of claim 8, wherein said at least one device includes a pair of leaflet devices applied to each valve leaflet, said devices being located at a coaptation surface of said valve leaflets proximate to commissures therebetween.

10. The heart valve prosthesis according to claim 8, wherein said at least one device includes at least one stitch applied to a prosthetic valve leaflet, said stitch providing a local deformation of said prosthetic valve leaflet, said at least one stitch being made of biodegradable or bioresorbable material.

11. The heart valve prosthesis according to claim 1, wherein said a bio-degradable or bio-resorbable material chosen from the group comprising 3-hydroxypropionic acid, polyylactic acid, poly caprolactone, poly glycolide, poly dioxanone, polytrimethyl carbonate, ε-polylysine, hyaluronic acid, poly saccharides and bioresorbable magnesium alloys.

* * * * *